United States Patent [19]

Pardhasaradhi et al.

[11] Patent Number: 5,728,848
[45] Date of Patent: Mar. 17, 1998

[54] 9-HYDROXYMETHYL-7,12 DIOXASPIRO[5,6] DODECANE, NOVEL 9-(2-HYDROXYETHYL-7,11-DIOXASPIRO[5,5]UNDECANE AND A PROCESS FOR PREPARING SAID 9-(2-HYDROXYETHYL-7,11 DIOXASPIRO [5,5] UNDECANE

[75] Inventors: Malladi Pardhasaradhi; Chembumkulam Kamalakshyamma Snehalatha Nair; Arsid Satyanarayana, all of Hyderabad, India

[73] Assignee: Council of Scientific & Industrial Research, New Delhi, India

[21] Appl. No.: 613,979

[22] Filed: Mar. 11, 1996

[51] Int. Cl.[6] .................. C07D 319/08; C07D 321/10
[52] U.S. Cl. .................................................. 549/333
[58] Field of Search ....................................... 549/333

[56] References Cited

U.S. PATENT DOCUMENTS 4,085,222  4/1978  Rhodes et al. ........................ 424/278

*Primary Examiner*—Johann Richter
*Assistant Examiner*—Laura L. Stockton
*Attorney, Agent, or Firm*—Shlesinger Arkwright & Garvey, LLP

[57] ABSTRACT

This invention relates to novel compounds namely 9-hydroxymethyl-7,12-dioxaspiro[5,6]dodecane and 9-(2-hydroxyethyl)-7, 11-dioxaspiro (5.5) undecane and a process for preparing 9-(2-hydroxyethyl)-7, 11-dioxaspiro (5.5) undecane which is employed as an intermediate in the synthesis of antiviral acyclonucleosides used in the treatment of herpes virus and HIV-1 infections.

2 Claims, 1 Drawing Sheet

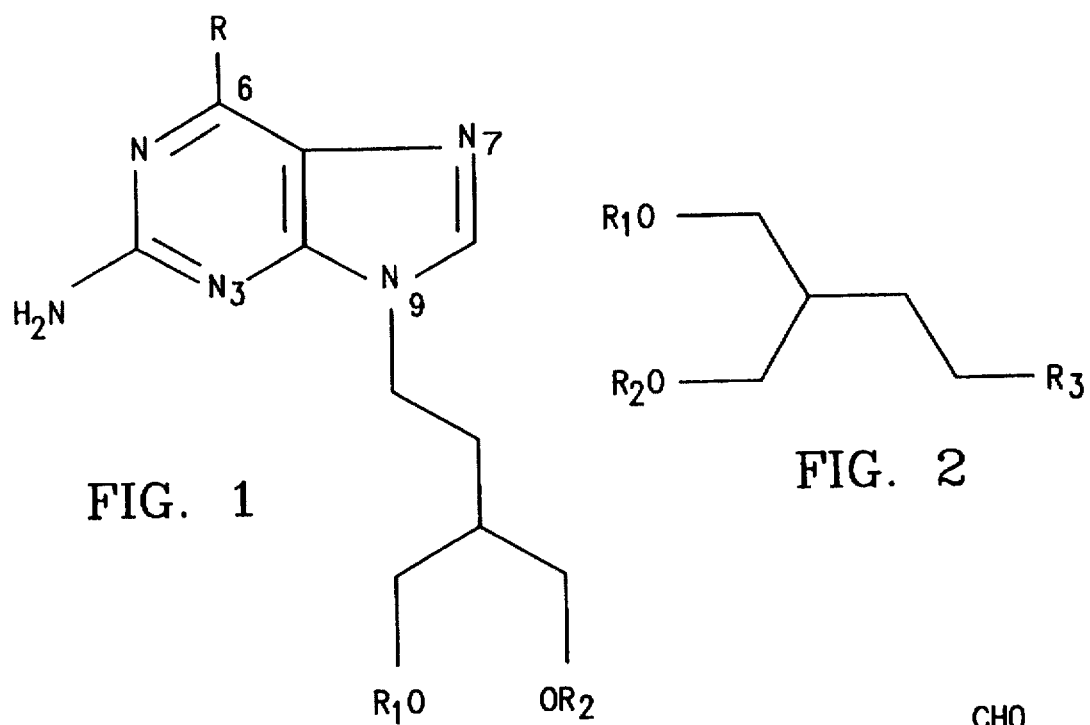
FIG. 1
FIG. 2
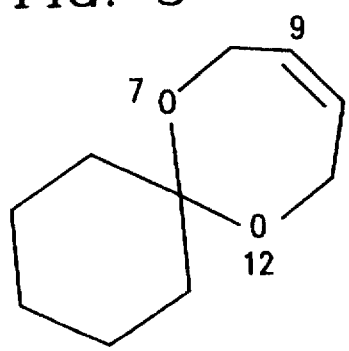
FIG. 3
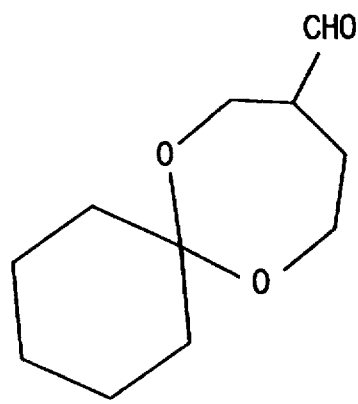
FIG. 4
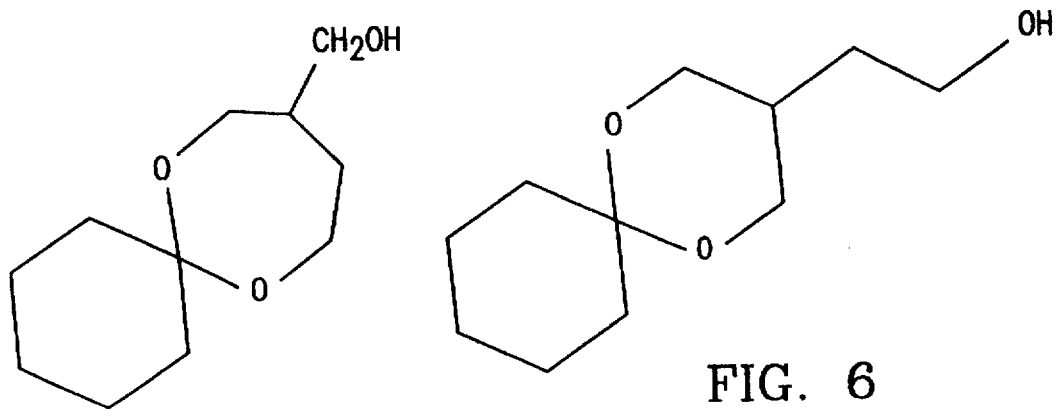
FIG. 5
FIG. 6

9-HYDROXYMETHYL-7,12 DIOXASPIRO[5,6] DODECANE, NOVEL 9-(2-HYDROXYETHYL-7,11-DIOXASPIRO[5,5]UNDECANE AND A PROCESS FOR PREPARING SAID 9-(2-HYDROXYETHYL-7,11 DIOXASPIRO [5,5] UNDECANE

FIELD OF THE INVENTION

This invention relates to novel compounds namely 9-hydroxymethyl-7,12-dioxaspiro[5,6]dodecane of formula V and 9-(2-hydroxyethyl)-7, 11-dioxaspiro (5.5) undecane of formula VI of the drawings accompanying the specification, and a process for preparing 9-(2-hydroxyethyl)-7, 11-dioxaspiro (5.5) undecane of formula VI of the drawings which is useful in the synthesis of antiviral acyclonucleosides used in the treatment of herpes virus and HIV-1 infections. The 9-(2-hydroxyethyl)-7, 11-dioxaspiro (5.5) undecane prepared by the process of the present invention has formula (VI) as shown in the drawing accompanying this specification and is useful in the synthesis of antiviral acyclonucleosides, viz. Penciclovir of formula 1 of the drawings enclosed with a specification wherein R=OH and $R_1=R_2=H$; and Eamciclovir of the formula I of the drawings wherein R=H and $R_1=R_2=Ac$.

BACKGROUND OF THE INVENTION

Penciclovir and Famciclovir are potent drugs used as virucides of herpes virus [Eur-Pat. Appl. FP352, 953. 31st Jan. 1990: GB Appl. 88 17.607.23 Jul. 1988. Nucleosides and Nucleotides, 1990 9 (4)499: Antiviral Chem. Chemother. 1993, 4(2)67]. The antiviral compounds viz. Penciclovir and Famciclovir are also used in the treatment of HIV-1 intentions [PCT Int. Appl. WO9200742, 23 Jan. 1992]. The intermediates of formula (II) of the drawings, wherein $R_1,R_2=H_3C)_2$ C. $R_3=Br$ or O-tosyl: or $R_1=R_2=Ac$ and $R_3=Br$ : which are required for the 9-N-alkyl substitution in the synthesis of Penciclovir and Famciclovir have been prepared by reducing triethyl-1, 1, 2-ethanetricarboxylate into 2-hydroxymethil butane-1, 4-diol [Tetrahedron] lett. 1985, 26(35)4265, PCT Int. Appl. WO 9113, 162. 05 Sep. 1991, GB Appl., 90/4, 647 01 Mar. 1990 followed by selective ketalizaton or acetylation. The novel compounds 9-hydroxymethyl-7,12-dioxaspiro[5,6] dodecane of formula V and 9-(2-hydroxyethyl)-7, 11-dioxaspiro (5.5) undecane of formula VI of the drawings can be used with advantage for the 9-N alkyl substitution of the purines in order to make antiviral drugs like penciclovir and famciclovir. They are only intermediates and an independent use of these intermediates are not very obvious.

In our continuous research work in the area of carbon-monoxide chemistry, it was found that the crucial intermediate 9-(2-hydroxyethyl)-7, 11-dioxaspiro [5,5] undecane of the formula (VI) of the drawings accompanying the specification, which is useful for the synthesis of Penciclovir and Famciclovir can be prepared more efficiently starting with cis-but-2-ene-1, 4-dio and cyclohexanone through the formation of 7, 12-dioxaspiro [5,6]dodec-9-ene of the formula (III) of the drawings accompanying the specification, 9-formyl-7, 12-dioxaspiro[5,6]dodecane of the formula (IV) of the drawings accompanying the specification and 9-hydroxymethyl-7, 12-dioxaspiro[5,6]dodecane of the formula (V) of the drawing accompanying the specification.

BRIEF DESCRIPTION OF THE DRAWINGS

FIG. 1 represents the formula for the antiviral acyclonucleosides according to the present invention;

FIG. 2 represents the formula for the intermediates used in the 9-N-alkyl substitution for synthesis of Penciclovir and Famciclovir;

FIG. 3 represents the formula for 7,12-dioxaspiro-[5,6] dodec-9-ene;

FIG. 4 represents the formula for 9-formyl-7,12-dioxaspiro[5,6] dodecane;

FIG. 5 represents the formula for 9-hydroxymethyl-7,12-dioxaspiro [5,6] dodecane; and FIG. 6 represents the formula for 9-(2-hydroxyethyl)-7, 11-dioxaspiro(5,5) undecane.

DETAILED DESCRIPTION OF THE PREFERRED EMBODIMENTS

Accordingly, the present invention provides an improved process for the preparation of 9(2-hydroxyethyl)-7, 11-diosaspiro[5,5]undecane of formula (VI) shown in the drawing accompanying this specification which is useful in the synthesis of antiviral acyclonucleosides used in the treatment of herpes virus and HIV-1 infections which comprises:

a. Reacting cis-but-2-ene-1, 4-diol with cyclohexanone in a non-polar solvent in the presence of a heterogeneous sulphonated nitro coal acid (SNCA) catalyst prepared by the process described herein below to obtain 7,12-dioxaspirol [5,6]dodec-9-ene of formula (III) of the drawings;

b. Reacting 7, 12-dioxaspiro[5,6]dodec-9-ene of formula (III) of the drawings with syngas under a pressure in the range of 80 to 130 bar, at a temperature in the range of 80° to 120° C. for a period in the range of 4 to 8 hrs, in the presence of RhH (CO) $(TPP)_3$ catalyst in a non-polar solvent to yield 9-formyl-7-12-dioxaspiro[5,6]dodecane of formula (IV) of the drawings;

c. Reducing 9-formyl-7, 12-dioxaspiro[5,6]dodecane of the formula (IV) of drawing with an agent capable of effecting reduction in the presence of an alcoholic solvent at a temperature in the range of 0° to 20° C. for a period in the range of 1 to 6 hrs to produce 9-hydroxymethil-7, 12-dioxaspiro[5,6]dodecane of the formula (V) of drawing; and d. Rearranging 9-hydroxymethyl-7, 12-dioxaspiro[5,6] dodecane of formula (V) of the drawing in the presence of an acidic catalyst and an organic solvent at a temperature in the range at 0° to 30° C. for a period ranging from 3 to 6 hrs to yield 9-(2-hydroxyethyl)-7, 11-dioxaspiro[5,5]undecane of formula (VI) of the drawings.

The novel sulfonated nitro coal acid (SNCA) which is used as a heterogeneous acid catalyst in step (a) of the above process is prepared from lignite. SNCA is prepared by oxidizing lignite powder using nitric acid to form nitro coal acid and thereafter, filtering and extracting the insoluble nitro coal acid and sulfonating the insoluble nitro coal acid using oleum to form the sulfonated nitro coal acid which is dried and purified by solvent extraction. The oxidation is effected at a temperature in the range of 25°–80° C. using nitric acid of concentration ranging from 20–60%, and the sulfonation step is effected at a temperature of 100°–150° C.

Preferably, SNCA catalyst formed is dried at a temperature range of 80°–130° C. and the solvent such as benzene, methanol and/or acetone, is used for the solvent extraction for purification of the catalyst.

Compound VI can be converted into 9-2-bromoethyl)-7, 11-dioxaspiro [5,5]-undecane which can be reacted with 2-amino-6-chloropurine by known methods to give antiviral acyclonucleosides. Since the preparation of the bromoderivative and its reaction with 2-amino-6-chloropurine involve well known methods reported in the literature, these procedures were not given in the present case. Likewise, RhH (CO) (TPP)$_3$ catalyst is a well known compound reported in the literature and hence only the structural formula is given in this case.

The non-polar solvents used may be selected from benzene, toluene and xylene and the like. However, the applicants notice that the reducing agent namely sodium borohydride used for reduction of the aldehyde to the corresponding alcohol is the best suited method. Other reducing agents either in neutral medium or under acedic conditions are not useful for this reduction in order to get high yields of the product.

The reducing agent used in step (c) above may be sodium borohydride and the like.

The catalyst used in step (d) may be P-toluene sulphonic acid, Amberlyst-15, and the like. The applicants have specifically selected P-toulene sulphonic acid as a homogenous catalyst and amberlyst-15 as a heterogeneous catalyst to effect the rearrangement reaction. Depending upon the catalyst one uses, the workup of the product differs. The arrangement can be brought about best by these two reagents with the workup procedures of the present invention.

Among the organic solvents, the chlorinated hydrocarbons, ethers and hydrocarbons are useful for the rearrangement reaction. The applicants exclude the possibility of using benzene as a solvent because of its carcinogenic character. Likewise, chlorohexane and other aliphatic solvents are not suitable for the present invention since alcohol is not going to be soluable in the medium.

The invention is illustrated in the examples given below, which should not be construed to limit the scope of the present invention. As generally adapted, the yields of the compounds are always expressed inmole percentage.

EXAMPLE 1

Cis-but-2-ene, 4-diol (50 g), cyclohexanone (50 g) and SNCA catalyst (2.5 g) were refluxed in benzene (75 ml) using a Deanstark water separator. The catalyst was filtered, the solvent evaporated and the residue distilled at 80°–85° C./4 torr to give 7,12-dioxaspiro[5,6]dodec-9-ene of formula III (92%) of the drawings.

7,12-dioxaspiro[5,6]dodec-9-ene of the formula III (70 g), toluene (70 ml), RhH(CO) (TPP)$_3$ catalyst (1.0 g) and triphenylphosphine (TPP, 2.3 g) were taken into an autoclave. It was pressurized to 130 bar with a mixture of CO H$_2$ and reacted at 100° C. for 4 hr. After releasing the pressure, the solvent was evaporated and 9-formyl-7, 12-dioxaspiro [5,6]dodecane of formula IV of the drawings enclosed with the specification was distilled at 100°–113° C./1 torr (93%).

To a solution of 9-formyl-7, 12-dioxaspiro[5,6]dodecane of formula IV (5 g) in methanol (15 ml) was added in small portions NaBH$_4$ (0.5 g) while stirring the solution and maintaining the temperature at 10° C. After complete addition, the reaction mixture was stirred for 3 hr at 20° C. The product residue obtained after evaporation of methanol was treated with water (20 ml), extracted into ether and dried over K$_2$CO$_3$. Evaporation of ether gave 9-hydroxymethyl-7, 12-dioxaspiro[5,6]dodecane of formula V (5 g) of the drawings as colorless viscous liquid.

A solution of 9-hydroxymethyl-7, 12-dioxaspiro[5,6] dodecane of the formula V (4 g) of the drawings in benzene (15 ml) was stirred at 10° C. for 5 hr with anhydrous p-toluenesulphonic acid (0.2 g). The reaction mixture was made alkaline by adding TEA and water. The benzene layer was separated and the aqueous layer extracted with benzene. The combined benzene solution was dried over K$_2$CO$_3$ and evaporate to a residue (4 g). It was chromatograped on silicagel using chloroform-methanol mixture as eluent to give 9-(2-hydroxyethyl)-7, 11-dioxaspiro[5,5]undecane of formula VI (2.8 g) (70%) of the drawings as colorless viscous liquid.

EXAMPLE 2

7,12-Dioxaspiro[5,6]Dodec-9-ene of formula III (70 g), toluene (140 ml), RhH(CO) (TPP)$_3$ catalyst (1.0 g) and triphenylphosphine (TPP, 2.3 g) were taken into an autoclave. It was pressurized to 90 bar with a mixture of CO and H$_2$ and reacted at 100° C. for 8 hr. After releasing the pressure the solvent was evaporated and the residue fractionated under vacuum to give 9-formyl-7, 12,-dioxaspiro [5,6]dodecane of formula IV (65%) of the drawings.

EXAMPLE 3

7,12-dioxaspiro[5,6]dodec-9-ene of formula III (50 g), toluene (100 ml), RhH(CO) (TPP)$_3$ catalyst (1.0 g) and triphenylphosphine (TPP, 3 g) were taken into an autoclave, It was pressurized to 130 bar with a mixture of CO and H$_2$ and reacted at 80° C. for 5 hr. After realizing the pressure, the solvent was evaporated and 9-formyl-7, 12-dioxaspiro [5,6]dodecane of formula IV of the drawings was distilled (85%).

FORMULA 4

A solution of 9-hydroxymethyl-7,12-dioxaspiro[5,6] dodecane of formula V (3 g) of the drawings in benzene (10 ml) was stirred at 10° C. for 8 hr with Amberlyst-15 catalyst (0.2 g). The benzene layer was decanted and the catalyst washed several times with benzene. The combined benzene extract was evaporated to give a residue (3 g). After chromatographic purification 9(2-hydroxyethtyl)-7, 11-dioxaspiro[5,5]undecane of formula VI of the drawing was obtained (60%).

We claim:

1. The compound:

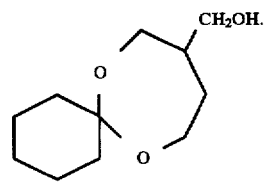

2. The compound:

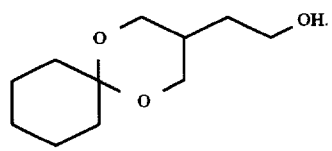

* * * * *